United States Patent
Gatfield et al.

(10) Patent No.: US 7,482,479 B2
(45) Date of Patent: *Jan. 27, 2009

(54) PRODUCTION OF CIS-PELLITORIN AND USE AS A FLAVOURING

(75) Inventors: Ian-Lucas Gatfield, Höxter (DE); Jakob Ley, Holzminden (DE); Jan Foerstner, Holzminden (DE); Gerhard Krammer, Holzminden (DE); Arnold Machinek, Holzminden (DE)

(73) Assignee: Symrise GmbH & Co., KG, Holzminden (DE)

(*) Notice: Subject to any disclaimer, the term of this patent is extended or adjusted under 35 U.S.C. 154(b) by 578 days.

This patent is subject to a terminal disclaimer.

(21) Appl. No.: 10/518,074

(22) PCT Filed: Jun. 20, 2003

(86) PCT No.: PCT/EP03/06545

§ 371 (c)(1), (2), (4) Date: Dec. 16, 2004

(87) PCT Pub. No.: WO04/000787

PCT Pub. Date: Dec. 31, 2003

(65) Prior Publication Data

US 2005/0234132 A1    Oct. 20, 2005

(30) Foreign Application Priority Data

Jun. 20, 2002  (DE) ................ 102 27 462

(51) Int. Cl.
*C07C 231/00* (2006.01)
(52) U.S. Cl. ........................ 554/69; 514/627

(58) Field of Classification Search ........... None
See application file for complete search history.

(56) References Cited

FOREIGN PATENT DOCUMENTS

| CA | 280972 | 1/1996 |
|---|---|---|
| WO | WO 97/04666 | 2/1997 |

OTHER PUBLICATIONS

Tanaka et al., Chemistry Letters, pp. 315-318, 1981.*
Tsukahara, Yuhko et al., "A Convenient Method For the Preparation of Conjugated Olefins From Allyli Acetates and Aldehydes. Synthesis of Pellitorine", Bulletin of the Chemical Society of Japan, (1984), 57(10), 3013-14.
Gedey S et al., "Sequential Resolution of Ethyl 3-aminobutyrate With Carboxylic Acid Esters By *Candida antarctica* Lipase B", Tetrahedron: Asymmetry, Elsevier Science Publishers, Amsterdam, NL, Bd. 10, Nr. 13, Jul. 2, 1999.
Saadali, Bouchra et al., "Alkamides From *Artemisia dracunculus*", Phytochemistry (2001), 58(7), 1083-1086.
Database FSTA 'Online! International Food Information Service (IFIS), Franfurt/Main, DE: Database accession No. 91-1-09-h0235, Horsky V.: Beverage based on Beer; Method of Manufacture, 1996.
Kollmannsberger H et al., "Saeureamide in Hochdruckextrakten Aus Muntokpfeffer Amides From Supercritical Fluid Extracts of Muntok-Pepper", Chemie Mikrobiologie, Technologie Der Lebensmittel, XX, XX, Bd. 14, NR. 3/4 , 1992, Seiten 87-94.

* cited by examiner

*Primary Examiner*—Deborah D Carr
(74) *Attorney, Agent, or Firm*—Roylance, Abrams, Berdo & Goodman, L.L.P.

(57) ABSTRACT

The invention describes a process for the production of 2E,4Z-decadienoic acid-N-isobutylamide (cis-pellitorine) and its use as a pungent principle and aromatic substance having a heat-generating effect, preferably in preparations used for foodstuffs, oral hygiene or luxury foodstuffs.

18 Claims, No Drawings

PRODUCTION OF CIS-PELLITORIN AND USE AS A FLAVOURING

The invention describes a process for the production of 2E,4Z-decadienoic acid-N-isobutylamide (cis-pellitorine) and its use as a pungent principle and aromatic substance having a heat-generating effect, preferably in preparations used for foodstuffs, oral hygiene or luxury foodstuffs. The invention also concerns preparations containing 2E,4Z-decadienoic acid-N-isobutylamide used for foodstuffs, oral hygiene or luxury foodstuffs.

Capsaicin [N-(4-hydroxy-3-methoxybenzyl)-8-methyl-(6E)-nonenoic acid amide, cf. structure 1, FIG. 1] and other capsaicinoids have been known as pungent-tasting and heat-generating aromatic substances derived from various types of capsicum, particularly chilli, since 1871. Heat-generating substances or substances having a heat-generating effect are understood to be those that create a sensation of heat. With an appropriately low dosage of capsaicinoids (the threshold value is a dilution of approx. $1:10^5$), only a pleasant, neutral pungency and feeling of warmth in the mouth is perceived. The problem with capsaicin is its high acute toxicity ($LD_{50}$ (mouse oral) 47 mg), which makes its usability in the preparation more difficult, and the chronic gastritis, kidney and liver damage that occur with frequent use and overdosing (Römpp Lexikon Naturstoffchemie, Thieme 1997, p. 109). Despite its good sensory properties, there is therefore a need for less problematic pungent principles. Although piperine (1-piperoyl piperidine, cf. structure 2, FIG. 1), which occurs in white pepper, also produces a pungent sensation (Römpp Lexikon Naturstoffchemie, Thieme 1997, p. 500), in comparison to capsaicin it displays a relative pungency of only around 1%. Furthermore, piperine has a strong inherent flavour, reminiscent of pepper, which means that it has only limited use in many preparations.

Figure 1

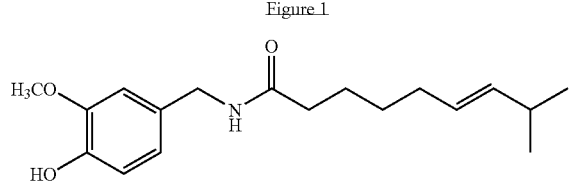

1

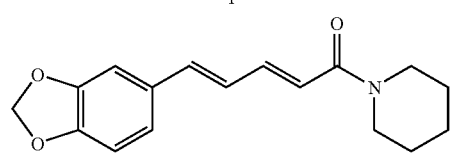

2

The object of the present invention was to identify naturally occurring substances having a pungent and/or heat-generating effect and an otherwise neutral aromatic profile, which can be used as aromatic substances in preparations used in foodstuffs or in luxury foodstuffs. A process for their simple, cost-effective and largely natural synthesis should also be developed.

The invention thus concerns the production of 2E,4Z-decadienoic acid-N-isobutyl-amide (cis-pellitorine), characterised in that a 2E,4Z-decadienoic acid ester is reacted with isobutylamine in the presence of a catalyst, preferably an enzyme, in particular an enzyme having lipase activity, the enzyme being in the form of a free protein or being associated with a support, the mixture with unreacted 2E,4Z-decadienoic acid ester optionally undergoes saponification, preferably with an enzyme in an aqueous medium or in a base diluted with water, particularly preferably in the aqueous solution of inorganic basic salts, the 2E,4Z-decadienoic acid that is formed is preferably separated off by extraction and then the mixture is isolated by physico-chemical methods, preferably by crystallisation, chromatography, distillation or co-distillation.

The method is clarified by means of the structural formula below:

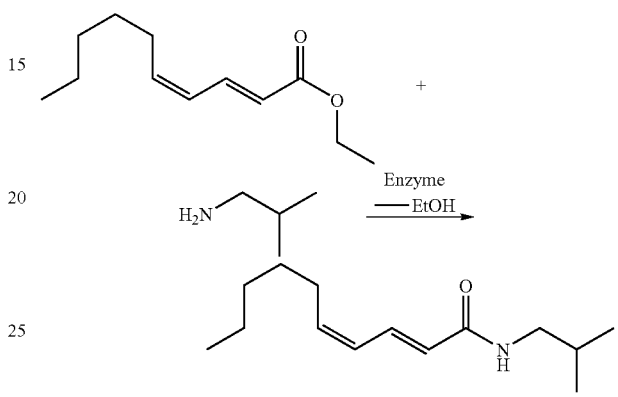

Surprisingly it was found that the process according to the invention allows very simple access to large, readily purified amounts of the desired 2E,4Z-decadienoic acid-N-isobutylamide. The synthesis described until now in the literature, on the other hand, is a multi-stage process; cis-pellitorine together with trans-pellitorine could be isolated in poor yields by thin-layer chromatography; the toxic selenium dioxide inter alia was used as a reagent in this synthesis (Bull. Chem. Soc. Jpn., 1984, Vol. 57, pages 3013ff.).

2E,4Z-decadienoic acid-N-isobutylamide within the meaning of the invention is pure 2E,4Z-decadienoic acid-N-isobutylamide or a mixture of at least 80 wt. % of 2E,4Z-decadienoic acid-N-isobutylamide and at least two other N-isobutylamides of decanoic acid, 2E-decenoic acid, 2E,4E-decadienoic acid, 2Z,4E-decadienoic acid, 2Z,4Z-decadienoic acid, 2E,4Z,7Z-decatrienoic acid, 3Z,5E-decadienoic acid or 3Z,5E,7Z-decatrienoic acid. The mixture according to the invention is novel.

2E,4Z-decadienoic acid esters within the meaning of the invention are esters of 2E,4Z-decadienoic acid and aliphatic monohydric alcohols having 1 to 20 C atoms, but in particular methanol, ethanol, 1-propanol, 2-propanol, 1-butanol, 2-butanol, 2-methyl-1-propanol, 2-methyl-2-propanol, 1-pentanol, 2-pentanol, 3-pentanol, 1-hexanol, 2-hexanol, 3-hexanol, 1-heptanol, 2-heptanol, 3-heptanol, 4-heptanol, 1-octanol, 2-octanol, 1-nonanol, 1-decanol, 1-undecanol, 1-dodecanol, 1-tridecanol, 1-tetradecanol, 1-pentadecanol, 1-hexadecanol, 1-heptadecanol, 1-octadecanol, 1-nonadecanol, 1-eicosanol or polyhydric alcohols having 2 to 18 C atoms such as ethylene glycol, 1,2-propylene glycol, 1,3-propylene glycol, glycerol, pentaerythritol, sugar alcohols such as erythritol, sorbitol, glucitol, mannitol, monosaccharides such as tetroses, e.g. erythrose or threose, pentoses, e.g. arabinose, ribose, lyxose, xylose, hexoses such as allose, altrose, galactose, mannose, gulose, idose, glucose, talose, fructose, oligosaccharides such as maltose, raffinose, sucrose, maltooligosaccharides or lactose, wherein the additional OH groups of the polyhydric alcohols can be esterified with aliphatic, saturated or unsaturated carboxylic acids or of mono- or polyhydroxy-substituted fatty acids, for example 8-hydroxy-5,6-octadienoic acid, which are esterified in turn with the aforementioned monohydric aliphatic alcohols or polyhydric alcohols.

Aliphatic, saturated or unsaturated carboxylic acids within the meaning of the invention are saturated or unsaturated linear carboxylic acids having 2 to 26 carbon atoms, but in particular acetic acid, propionic acid, butyric acid, pentanoic acid, hexanoic acid, heptanoic acid, octanoic acid, nonanoic acid, 2E-nonenoic acid, decanoic acid, 2E-decenoic acid, 2E,4E-decadienoic acid, 2E,4Z-decadienoic acid, 2E,4Z,7Z-decatrienoic acid, 3Z,5E-decadienoic acid, the stereoisomers of 4,5-dihydroxy-2-decenoic acid, the stereoisomers of 4,5-epoxy-2-decenoic acid, 3Z,5E,7Z-decatrienoic acid, deca-2,8-diene-4,6-diynoic acid, deca-2-ene-4,6,8-triynoic acid, undecanoic acid, dodecanoic acid, tridecanoic acid, tetradecanoic acid, pentadecanoic acid, hexadecanoic acid, 9E- or 9Z-hexadecenoic acid, heptadecanoic acid, octadecanoic acid, 9E- or 9Z- or 11E- or 11Z-octadecenoic acid, the various geometric isomers of 9,12-octadecadienoic acid, of 6,9,12-octadecatrienoic acid, of 9,12,15-octadecatrienoic acid, of 6,9,12,15-octadecatetraenoic acid, nonadecanoic acid, eicosanoic acid, the various geometric isomers of eicosaenoic acid, of 11,14-eicosadienoic acid, of 8,11,14-eicosatrienoic acid, of 5,8,11,14-eicosatetraenoic acid, of 5,8,11,14,17-eicosapentaenoic acid, of 10,13,16-docosatrienoic acid, of 7,10,13,16-docosatetraenoic acid, of 4,7,10,13,16-docosapentaenoic acid and of 4,7,10,13,16,19-docosahexaenoic acid.

2E,4Z-decadienoic acid esters within the meaning of the invention can preferably take the form of natural or enriched processed triglycerides, obtained for example from fatty oils of stillingia (*Sapium sebiferum*), *Sebastiana ligustra* or *Sebastiana commersoniana*), or of methyl or ethyl esters. Particularly preferred is a $C_{10}$ fraction obtained by enzymatic interesterification of stillingia oil in ethanol and subsequent distillation, characterised in that it contains at least 80 wt. % of ethyl-2E,4Z-decadienoate.

Surprisingly, in contrast to the isomeric 2E,4E-decadienoic acid-N-isobutylamide, in sensory testing the 2E,4Z-decadienoic acid-N-isobutylamide according to the invention has a pleasant, extremely pungent and warm flavour impression, which is reminiscent of ethanol and is relatively long lasting. No other sensory impressions can be detected, so the profile is very neutral.

The natural occurrence of trans-pellitorine (2E,4E-decadienoic acid-N-isobutylamide) has been described many times in the literature. The amide is relatively widespread and occurs for example in pepper (overview by G. M. Strunz, Stud. Nat. Prod. Chem. 2000, Volume 24 (Bioactive Natural Products (Part E)), page 683-738). Its sensory impression has been described as primarily numbing (cf. for example J. Agric. Food Chem., 1981, Volume 29, pages 115ff. or Fitoterapia, 2001, Volume 72, pages 197ff.), as was also able to be demonstrated in internal comparative tests.

By contrast, 2E,4Z-decadienoic acid-N-isobutylamide has only recently been found in tarragon, as described in Phytochemistry, 2001, Volume 58, pages 1083-1086.

The invention therefore also concerns the use of 2E,4Z-decadienoic acid isobutylamide as an aromatic substance, preferably as a pungent principle or aromatic substance having a heat-generating effect, particularly preferably as a pungent principle or aromatic substance having a heat-generating effect in preparations used for foodstuffs, oral hygiene or luxury foodstuffs.

The present invention also provides preparations, semi-finished products and perfume, aromatic and flavouring compositions containing 2E,4Z-decadienoic acid-N-isobutylamide.

2E,4Z-decadienoic acid-N-isobutylamide can naturally also be used in cosmetic or dermatological preparations for heat generation on the skin.

In a particularly preferred embodiment of the invention, 2E,4Z-decadienoic acid-N-isobutylamide is used in combination with other pungent-tasting and/or heat-generating substances or pungent-tasting plant extracts. A particularly rounded sensory profile can be obtained in this way. In particular the combination of 2E,4Z-decadienoic acid-N-isobutylamide with a pungent-tasting plant extract in the ratio 0.01 to 1 to 100 to 1, preferably 0.1 to 1 to 10 to 1, produces a pleasant sensory profile.

Other pungent-tasting and/or heat-generating substances can be, for example, capsaicin, dihydrocapsaicin, gingerol, paradol, shogaol, piperine, carboxylic acid-N-vanillylamides, in particular nonanoic acid-N-vanillylamide, 2-alkenoic acid amides, particularly 2-nonenoic acid-N-isobutylamide, pellitorine or spilanthol, 2-nonenoic acid-N-4-hydroxy-3-methoxyphenylamide, alkyl ethers of 4-hydroxy-3-methoxybenzyl alcohol, in particular 4-hydroxy-3-methoxybenzyl-n-butyl ether, alkyl ethers of 4-acyloxy-3-methoxybenzyl alcohol, in particular 4-acetyloxy-3-methoxybenzyl-n-butyl ether and 4-acetyloxy-3-methoxybenzyl-n-hexyl ether, alkyl ethers of 3-hydroxy-4-methoxybenzyl alcohol, alkyl ethers of 3,4-dimethoxybenzyl alcohol, alkyl ethers of 3-ethoxy-4-hydroxybenzyl alcohol, alkyl ethers of 3,4-methylene dioxybenzyl alcohol, (4-hydroxy-3-methoxyphenyl) acetic acid amides, in particular (4-hydroxy-3-methoxyphenyl) acetic acid-N-n-octylamide, ferulic acid phenethyl amides, nicotinaldehyde, methyl nicotinate, propyl nicotinate, 2-butoxyethyl nicotinate, benzyl nicotinate, 1-acetoxychavicol, polygodial or isodrimeninol.

Pungent-tasting plant extracts can be all plant extracts suitable for food use, which give rise to a pungent or warm sensory impression. Preferred pungent-tasting plant extracts are for example pepper extract (*Piper* ssp., in particular *Piper nigrum*), water pepper extract (*Polygonum* ssp., in particular *Polygonum hydropiper*), extracts from *Allium* ssp. (in particular onion and garlic extracts), extracts from radish (*Raphanus* ssp.), horseradish extracts (*Cochlearia armoracia*), extracts from black (*Brassica nigra*), wild or yellow mustard (*Sinapis* ssp., in particular *Sinapis arvensis* and *Sinapis alba*), pellitory extracts (*Anacyclus* ssp., in particular *Anacyclus pyrethrum* L.), coneflower extracts (*Echinaceae* ssp.), extracts from szechuan pepper (*Zanthoxylum* ssp., in particular *Zanthoxylum piperitum*), spilanthes extract (*Spilanthes* ssp., in particular *Spilanthes acmella*), chilli extract *Capsicum* ssp., in particular *Capsicum frutescens*), grains of paradise extract (*Aframomum* ssp., in particular *Aframomum melegueta* [rose] K. Schum.), ginger extract (*Zingiber* ssp., in particular *Zingiber officinale*) and galangal extract (*Kaempferia galanga* or *Alpinia galanga*).

The pungent-tasting plant extracts can be obtained from the corresponding fresh or dried plants or plant parts, but particularly from white, green or black peppercorns, water peppercorns, onions and garlic, radish roots, horseradish, mustard seeds, coneflower roots, pellitory, plant parts of the *Zanthoxylum* species, plant parts of the spilanthes species, chilli pods, grains of paradise or ginger or galangal roots, in such a way that the dried plant parts, which have preferably first been crushed, are extracted with a solvent suitable for foodstuffs and luxury foodstuffs, but preferably with ethanol, water, hexane or heptane or ethanol/water mixtures, at 0° C. up to the boiling point of the particular solvent or mixture, then filtered and the filtrate wholly or partially concentrated to low volume, preferably by distillation, freeze drying or spray drying. The raw extract obtained in this way can then also undergo further processing, for example steam treatment under pressures of 0.01 mbar to normal pressure, and/or be taken up in a solvent suitable for foodstuffs and luxury foodstuffs.

A solvent suitable for foodstuffs and luxury foodstuffs can be, for example: water, ethanol, methanol, propylene glycol, glycerol, acetone, dichloromethane, diethyl ether, hexane, heptane, triacetin, vegetable oils or fats, or supercritical carbon dioxide or mixtures of the aforementioned solvents.

The invention also provides preparations used for foodstuffs or luxury foodstuffs, containing 2E,4Z-decadienoic acid-N-isobutylamide in an effective amount and optionally other conventional basic substances, auxiliary substances and additives for foodstuffs and luxury foodstuffs. They generally contain 0.000001 wt. % to 10 wt. %, preferably 0.0001 to 1 wt. %, but in particular 0.0001 wt. % to 0.1 wt. %, relative to the total weight of the preparation, of 2E,4Z-decadienoic acid-N-isobutylamide. Other conventional basic substances, auxiliary substances and additives for foodstuffs or luxury foodstuffs can be included in quantities of 0.000001 to 99.999999 wt. %, preferably 10 to 80 wt. %, relative to the total weight of the preparation. The preparations can also display water in a quantity of up to 99.999999 wt. %, preferably 5 to 80 wt. %, relative to the total weight of the preparation.

The preparations used for foodstuffs or luxury foodstuffs within the meaning of the invention are for example baked goods (e.g. bread, dry biscuits, cakes, other pastries), confectionery (e.g. chocolates, fruit gums, hard and soft caramels, chewing gum), alcoholic or non-alcoholic drinks (e.g. coffee, tea, wine, wine-based drinks, beer, beer-based drinks, liqueurs, spirits, brandies, fruit-based soft drinks, isotonic drinks, soft drinks, nectars, fruit and vegetable juices, fruit or vegetable juice preparations), instant drinks, meat products (e.g. ham, sausage or uncured sausage preparations), eggs or egg products (dried egg, egg white, egg yolk), cereal products (e.g. breakfast cereals, muesli bars), dairy products (e.g. milk drinks, ice cream, yoghurt, kefir, cream cheese, soft cheese, hard cheese, dried milk powder, whey, butter, buttermilk), fruit preparations (e.g. jams, fruit sorbets, fruit sauces), vegetable preparations (e.g. ketchup, sauces, dried vegetables), snacks (e.g. baked or fried potato crisps or potato dough products, extruded products based on maize or peanuts), products based on fats or oils or emulsions thereof (e.g. mayonnaise, remoulade, dressings), ready meals and soups, spices, spice mixes and in particular seasonings, which are used in the snacks sector. The preparations within the meaning of the invention can also be used as semi-finished products for the production of other preparations used for foodstuffs or luxury foodstuffs. The preparations within the meaning of the invention can also take the form of capsules, tablets (uncoated and coated tablets, e.g. stomach acid-resistant coatings), pastilles, granules, pellets, solids mixtures, dispersions in the liquid phase, emulsions, powders, solutions, pastes or other swallowable or chewable preparations as food supplements.

It has particularly advantageously also been found that 2E,4Z-decadienoic acid-N-isobutylamide, in particular the combination according to the invention of 2E,4Z-decadienoic acid-N-isobutylamide with pungent-tasting plant extracts, can imitate the pungent flavour of alcohol in alcoholic drinks or preparations made from alcoholic drinks, so that the alcohol content in alcoholic drinks or in preparations made from alcoholic drinks can be reduced whilst retaining the same sensory assessment.

It has particularly advantageously also been found that 2E,4Z-decadienoic acid-N-isobutylamide can imitate the pungent flavour of capsaicin, dihydrocapsaicin and nonivamide, so that the capsaicin content in preparations used for foodstuffs or luxury foodstuffs can be reduced whilst retaining the same sensory assessment.

A further preferred embodiment of the invention are preparations used for oral hygiene, in particular dental care products such as toothpastes, tooth gels, tooth powders, mouthwashes, chewing gums and other oral care products, containing 2E,4Z-decadienoic acid-N-isobutylamide in an effective amount and optionally other conventional basic substances, auxiliary substances and additives for such preparations. They generally contain 0.000001 wt. % to 10 wt. %, preferably 0.0001 to 1 wt. %, but in particular 0.0001 wt. % to 0.1 wt. %, relative to the total weight of the preparation, of 2E,4Z-decadienoic acid-N-isobutylamide. Other conventional basic substances, auxiliary substances and additives for preparations used for oral hygiene can be included in quantities of 0.000001 to 99.999999 wt. %, preferably 10 to 80 wt. %, relative to the total weight of the preparation. The preparations can also display water in a quantity of up to 99.999999 wt. %, preferably 5 to 80 wt. %, relative to the total weight of the preparation.

Dental care products containing 2E,4Z-decadienoic acid-N-isobutylamide generally consist of an abrasive system (grinding or polishing agent), such as e.g. silicas, calcium carbonates, calcium phosphates, aluminium oxides and/or hydroxyl apatites, of surface active substances, such as e.g. sodium lauryl sulfate, sodium lauryl sarcosinate and/or cocamidopropyl betaine, of moisture retainers, such as e.g. glycerol and/or sorbitol, of thickening agents, such as e.g. carboxymethylcellulose, polyethylene glycols, carrageenans and/or Laponites®, of sweeteners, such as e.g. saccharine, of stabilisers and of active ingredients, such as e.g. sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetyl pyridinium chloride, aluminium lactate, potassium citrate, potassium nitrate, potassium chloride, strontium chloride, hydrogen peroxide, flavourings and/or sodium bicarbonate.

Chewing gums containing 2E,4Z-decadienoic acid-N-isobutylamide generally consist of a chewing gum base, in other words a chewing compound that becomes plastic when chewed, of sugars of various types, sugar substitutes, sweeteners, sugar alcohols, moisture retainers, thickeners, emulsifiers, flavourings and stabilisers.

The preparations according to the invention containing 2E,4Z-decadienoic acid-N-isobutylamide can be produced in such a way that 2E,4Z-decadienoic acid-N-isobutylamide is incorporated into the preparations used for foodstuffs, oral hygiene or luxury foodstuffs as a substance, as a solution or in the form of a mixture with a solid or liquid carrier. The preparations according to the invention, containing 2E,4Z-decadienoic acid-N-isobutylamide, in the form of solutions, can also advantageously be converted into a solid preparation by spray drying.

In order to produce the preparations, in a further preferred embodiment the 2E,4Z-decadienoic acid-N-isobutylamide and optionally other constituents of the preparation according to the invention can also be incorporated in advance in emulsions, in liposomes, e.g. starting from phosphatidyl cholin, in microspheres, in nanospheres or in capsules made from a matrix suitable for foodstuffs and luxury foodstuffs, e.g. made from starch, starch derivatives, other polysaccharides, natural fats, natural waxes or proteins, e.g. gelatine. A further embodiment consists in complexing 2E,4Z-decadienoic acid isobutylamide in advance with suitable complexing agents, for example with cyclodextrins or cyclodextrin derivatives, preferably β-cyclodextrin, and using it in this form.

As other constituents for the preparations according to the invention used for foodstuffs or luxury foodstuffs, other conventional basic substances, auxiliary substances and additives for foodstuffs or luxury foodstuffs can be used, e.g. water, mixtures of fresh or processed, plant-based or animalbased basic substances or raw materials (e.g. raw, roast, dried, fermented, smoked and/or boiled meat, egg, bone, gristle, fish, crustaceans and shellfish, vegetables, fruit, herbs, nuts, vegetable or fruit juices or pastes or mixtures thereof), digestible or indigestible carbohydrates (e.g. sucrose, maltose, fructose, glucose, dextrin, amylose, amylopectin, inulin, xylan, cellulose), sugar alcohols (e.g. sorbitol, mannitol, xylitol), natural or hydrogenated fats (e.g. tallow, lard, palm oil, coconut butter, hydrogenated vegetable fat), fatty oils (e.g. sunflower oil, groundnut oil, maize oil, safflower oil, olive oil, walnut oil, fish oil, soya oil, sesame oil), fatty acids or salts thereof (e.g. potassium stearate, potassium palmitate), proteinogenic or non-proteinogenic amino acids and related compounds (e.g. taurin, creatin, creatinin), peptides, native or processed proteins (e.g. gelatine), enzymes (e.g. peptidases, glucosidases, lipases), nucleic acids, nucleotides (inositol phosphate), flavour-enhancing substances (e.g. sodium glutamate, 2-phenoxypropionic acid), emulsifiers (e.g. lecithins, diacyl glycerols), stabilisers (e.g. carageenan, alginate, locust bean gum, guar gum), preservatives (e.g. benzoic acid, sorbic acid), antioxidants (e.g. tocopherol, ascorbic acid), chelating agents (e.g. citric acid), organic or inorganic acidulators (e.g. malic acid, acetic acid, citric acid, tannic acid, phosphoric acid), bitter principles (e.g. quinine, caffeine, limonine), sweeteners. (e.g. saccharine, cyclamate, aspartame, neotame, neohesperidin dihydrochalcone), mineral salts (e.g. sodium chloride, potassium chloride, magnesium chloride, sodium phosphate), substances preventing enzymatic browning (e.g. sulfite, ascorbic acid), ethereal oils, plant extracts, natural or synthetic dyes or coloured pigments (e.g. carotinoids, flavonoids, anthocyans, chlorophyll and derivatives thereof), herbs, as well as perfumes, synthetic, natural or nature-identical aromatic substances and flavourings.

The preparations according to the invention can preferably also contain an aromatic composition to round off and improve the flavour and/or aroma of the preparation. Suitable aromatic compositions contain for example synthetic, natural or nature-identical aromatic substances and perfumes, but in particular also other pungent-tasting and/or heat-generating substances or plant extracts.

The invention also provides the use of the preparations according to the invention as semi-finished products for the aromatisation of preparations manufactured therefrom as finished products.

EXAMPLES

Example 1

Preparation of 2E,4Z-decadienoic acid-N-isobutylamide (cis-pellitorine) by Enzymatic Reaction with ethyl-2E,4Z-decadienoate 10 g of ethyl-2E,4Z-decadienoate, 4.7 g of Chirazyme L-2 (c.f., C2, lyo., catalogue no. 1859242, Roche Diagnostics, Basle, Switzerland), 4 g of isobutylamine were stirred for 4 days at 55° C. 100 ml of diethyl ether were added to the batch and it was filtered; the filtrate was concentrated by evaporation in vacuo (crude yield 15.2 g). The product was stirred in 10% KOH/methanol (1:1 mixture) for 45 minutes at room temperature, extracted with ether, the ethereal phase dried over sodium sulfate, filtered and the filtrate concentrated by evaporation. The crude product was chromatographed on silica gel 60 (eluent hexane/ethyl acetate 10:1). Yield 9.1 g (GC: 99.4%); $^1$H-NMR (CDCl$_3$; 200 MHz): 7.56 (1H, ddd, 11.5 Hz, 14.9 Hz, 1.0 Hz), 6.08 (1H, dddd, 11.5 Hz, 10.8 Hz, 1.4 Hz, 0.6 Hz), 5.82 (1H, d, 11.5 Hz), 5.79 (1H, dtd, 10.8 Hz, 7.8 Hz, 0.9 Hz), 5.50 (1H, bs), 3.18 (2H, dd, 6.8 Hz, 6.1 Hz), 2.36-2.22 (2H, m), 1.81 (1H, m, 6.7 Hz), 1.50-1.22 (6H, m), 0.93 (6H, d, 6.7 Hz), 0.88 (3H, m) ppm; $^{13}$C-NMR (CDCl$_3$; 50 MHz): 166.34 (C), 140.07 (CH), 135.76 (CH), 126.28 (CH), 123.78 (CH), 46.96 (CH$_2$), 31.41 (CH$_2$), 29.14 (CH$_2$), 28.63 (CH), 28.15 (CH$_2$), 22.52 (CH$_2$), 20.15 (CH$_3$), 14.02 (CH$_3$) ppm.

Example 2

Preparation of Technical 2E,4Z-decadienoic acid-N-isobutylamide (cis-pellitorine) by Enzymatic Reaction with ethyl-2E,4Z-decadienoate in Toluene 100 g of ethyl-2E,4Z-decadienoate and 40 g of Chirazyme L-2 (c.f., C2, lyo., catalogue no. 1859242, Roche Diagnostics, Basle, Switzerland) were placed in 50 ml of toluene and 40 g of isobutylamine were added in portions with stirring for 4 days at 55° C. After filtration and gentle removal of the toluene by distillation in vacuo, a product containing 81% cis-pellitorine (GC) is obtained.

Example 3

Preparation of a Preparation Containing 2E,4Z-decadienoic acid-N-isobutylamide (cis-pellitorine) by Enzymatic Reaction with Stillingia Oil 100 g of stillingia oil, 20 g of Chirazyme L-2 (c.f., C2, lyo., catalogue no. 1859242, Roche Diagnostics, Basle, Switzerland) and 40 g of isobutylamine were stirred for 72 hours at 45° C. and the enzyme removed by filtration. The crude product (116 g) contains 2.5% (GC) of cis-pellitorine. Approx. 50 g of a fraction with 6.2% cis-pellitorine could be obtained from this by molecular distillation (0.12 mbar, 150° C.) and a new approximately 12 g fraction with 17.5% cis-pellitorine obtained by renewed molecular distillation of this fraction.

Example 4

Preparation of 2E,4E-decadienoic acid-N-isobutylamide (Trans-Pellitorine) (Comparison)

277 mg of 2E,4Z-decadienoic acid-N-isobutylamide from Example 1 were stirred with 29 mg of iodine in 10 ml of toluene for one hour at room temperature. The mixture was chromatographed on silica gel 60 with the eluent hexane/ethyl acetate 5:1. Yield: 61 mg (>95%, NMR); $^1$H-NMR (CDCl$_3$; 200 MHz): 7.19 (1H, dd, 14.9 Hz, 9.7 Hz), 6.13 (1H, dd, 15.1 Hz, 9.6 Hz), 6.07 (1H, dd, 15.1 Hz, 6.4 Hz), 5.75 (1H, d 14.9 Hz), 5.50 (1H, bs), 3.17 (2H, dd, 6.9 Hz, 6.1 Hz), 2.14 (2H, dd, 7 Hz, 6.4 Hz), 1.80 (1H, m, 6.7 Hz), 1.42 (2H, m, 7.1 Hz), 1.37-1.22 (4H, m), 0.93 (6H, d, 6.7 Hz), 0.89 (3H, m) ppm.

Example 5

Tasting of Cis-Pellitorine

The substance to be tasted is dissolved in ethanol and the ethanolic solution then diluted with an 11% sugar solution (final concentration: c). Approx. 5 ml of the sugar solution at a time are swallowed for the tasting. If the threshold value of the substance is known, a value just above the threshold value is chosen for the tasting. A group of 6 to 8 testers tasted the solutions.

a) Profile of 2E,4Z-decadienoic acid-N-isobutylamide (cis-pellitorine):

c=10 ppm: pronounced feeling of warmth, immediately pungent, typical alcohol pungency.

COMPARATIVE EXAMPLES b) Profile of dihydrocapsaicin:

c=100 ppb: slightly delayed onset of effect in the pharynx, burning, aggressive, no heat development.

c) Profile of 2E,4E-decadienoic acid-N-isobutylamide (trans-pellitorine):

c=10 ppm: saliva-stimulating, oily, fruity, slightly tingling, not pungent

Example 6

Use in an Apple Schnapps as an Alcohol Intensifier

| 14.90 l | alcohol 96 vol. % |
| 5.2 l | flavouring (natural apple fruit juice liqueur flavouring, 15 vol. %, contains 0.01 wt. % cis-pellitorine) |
| 27 kg | sugar syrup |
| 1 kg | citric acid monohydrate |

Top up with demineralised water to 100 l; total quantity 100 l

Example 7

Use in Combination with a Pungent Plant Extract as an Alcohol Intensifier

| 14.90 l | alcohol 96 vol. % |
| 5.2 l | flavouring (natural apple fruit juice liqueur flavouring, 15 vol. %, contains 0.0025 wt. % cis-pellitorine and 0.0075 wt. % grains of paradise extract) |
| 27 kg | sugar syrup |
| 1 kg | citric acid monohydrate |

Top up with demineralised water to 100 l; total quantity 100 l

Example 8

Use as an Aromatic Substance in a Toothpaste

| Part | Ingredient | Use in wt. % |
| --- | --- | --- |
| A | Demineralised water | 22.00 |
|   | Sorbitol (70%) | 45.00 |
|   | Solbrol ® M, sodium salt (Bayer AG, p-hydroxybenzoic acid alkyl ester) | 0.15 |
|   | Trisodium phosphate | 0.10 |
|   | Saccharine, 450 times | 0.20 |
|   | Sodium monofluorophosphate | 1.12 |
|   | Polyethylene glycol 1500 | 5.00 |
| B | Sident 9 (abrasive silicon dioxide) | 10.00 |
|   | Sident 22 S (thickening silicon dioxide) | 8.00 |
|   | Sodium carboxymethylcellulose | 0.90 |
|   | Titanium dioxide | 0.50 |
| C | Demineralised water | 4.53 |
|   | Sodium lauryl sulfate | 1.50 |
| D | Flavouring, containing 0.1% cis-pellitorine | 1 |

The ingredients in parts A and B are each premixed and stirred together well under vacuum at 25 to 30° C. for 30 minutes. Part C is premixed and added to A and B; D is added and the mixture is stirred well under vacuum at 25 to 30° C. for 30 minutes. After releasing the vacuum, the toothpaste is ready and can be filled.

Example 9

Use as an Aromatic Substance in a Sugar-Free Chewing Gum

| Part | Ingredient | Use in wt. % |
| --- | --- | --- |
| A | Chewing gum base, "Jagum T" | 30.00 |
| B | Sorbitol, powdered | 39.00 |
|   | Isomalt ® (Palatinit GmbH) | 9.50 |
|   | Xylitol | 2.00 |
|   | Mannitol | 3.00 |
|   | Aspartame ® | 0.10 |
|   | Acesulfame ® K | 0.10 |
|   | Emulgum ® (Colloides Naturels, Inc.) | 0.30 |
| C | Sorbitol, 70% | 14.00 |
|   | Glycerol | 1.00 |
| D | Flavouring, containing 0.1% cis-pellitorine | 1 |

Parts A to D are mixed and compounded intensively. The crude compound can be processed into ready-to-use chewing gum in the form of thin strips, for example.

Example 10

Use as an Aromatic Substance in a Mouthwash

| Part | Ingredient | Content (%) |
| --- | --- | --- |
| A | Ethanol | 10.00 |
|   | Cremophor ® CO 40 (BASF, detergent) | 1.00 |
|   | Benzoic acid | 0.12 |
|   | Flavouring, containing 0.4% cis-pellitorine | 0.25 |
| B | Demineralised water | 83.46 |
|   | Sorbitol, 70% | 5.00 |
|   | Sodium saccharine 450 | 0.07 |
|   | L-Blue 5000 e.c., 1% in water (dye) | 0.10 |

The ingredients in parts A and B are each mixed together. Part B is slowly stirred into part A until the mixture is homogeneous.

The invention claimed is:

1. Process for the production of 2E,4Z-decadienoic acid-N-isobutylamide (cis-pellitorine), characterised in that a 2E,4Z-decadienoic acid ester is reacted with isobutylamine in the presence of an enzyme catalyst, and then isolating the mixture by physico-chemical methods.

2. A sensory ingredient mixture containing at least 80 wt. % of 2E,4Z-decadienoic acid-N-iso-butylamide and at least two other N-isobutylamides of decanoic acid, 2E-decenoic acid, 2E,4E-decadienoic acid, 2Z,4E-decadienoic acid, 2Z,4Z-decadienoic acid, 2E,4Z,7Z-decatrienoic acid, 3Z,5E-decadienoic acid or 3Z,5E,7Z-decatrienoic acid.

3. A sensory agent comprising 2E,4Z-decadienoic acid-N-isobutylamide or a mixture according to claim 2 as an aromatic substance.

4. A sensory agent according to claim 3, wherein said aromatic substance comprises a pungent principle or aromatic substance having a heat-generating effect.

5. A food stuff preparation comprising a sensory agent according to claim 3.

6. An oral hygiene composition comprising a sensory agent according to claim 3.

7. Preparations useful for foodstuffs, oral hygiene or luxury foodstuffs, containing 2E,4Z-decadienoic acid isobutylamide or a mixture comprising at least 80 wt. % of 2E,4Z-decadienoic acid-N-isobutylamide and at least two other N-isobutylamides of decanoic acid, 2E-decenoic acid, 2E,4E-decadienoic acid, 2Z,4E-decadienoic acid, 2Z,4Z-decadienoic acid, 2E,4Z,7Z-decatrienoic acid, 3Z,5E-decadienoic acid or 3Z,5E,7Z-decatrienoic acid.

8. Preparations according to claim 7, containing at least one other pungent-tasting or heat-generating substance.

9. Preparations according to claim 7, containing at least one pungent-tasting plant extract.

10. Preparations according to claim 7, containing at least one other pungent-tasting or heat-generating substance and at least one pungent-tasting plant extract.

11. Preparations according to claim 7 in the form of a semi-finished product.

12. Preparations according to claim 7 in the form of a perfume, an aromatic composition, a flavouring composition, and a spice mix.

13. Preparations according to claim 7 containing at least 80 wt. % of 2E,4Z-decadienoic acid-N-isobutylamide and at least two other N-isobutylamides of decanoic acid, 2E-decenoic acid, 2E,4E-decadienoic acid, 2Z,4E-decadienoic acid, 2Z,4Z-decadienoic acid 2E,4Z,7Z-decatrienoic acid, 3Z,5E-decadienoic acid or 3Z,5E,7Z-decatrienoic acid.

14. Preparations according to claim 7 containing 2E,4Z-decadienoic acid-N-iso-butylamide.

15. The process of claim 1, further comprising saponifying unreacted 2E,4Z-decadienoic acid ester.

16. The process of claim 1, wherein the catalyst is an enzyme having lipase activity.

17. The process of claim 16, wherein the enzyme is on a support.

18. The process of claim 1, wherein the mixture is isolated by a process selected from the group consisting of crystallization, chromatography, distillation and co-distillation.

* * * * *